United States Patent [19]
Bailey

[11] Patent Number: 5,503,555
[45] Date of Patent: *Apr. 2, 1996

[54] DENTAL PROPHYLAXIS ANGLE

[75] Inventor: Ronald L. Bailey, Harvester, Mo.

[73] Assignee: Young Dental Manufacturing Company, Earth City, Mo.

[ * ] Notice: The term of this patent shall not extend beyond the expiration date of Pat. No. 5,156,547.

[21] Appl. No.: 224,263

[22] Filed: Apr. 7, 1994

Related U.S. Application Data

[63] Continuation of Ser. No. 963,132, Oct. 19, 1992, Pat. No. 5,328,369, which is a continuation-in-part of Ser. No. 613,366, Nov. 15, 1990, Pat. No. 5,156,547.

[51] Int. Cl.$^6$ .............................. A61C 1/08; A61C 3/06
[52] U.S. Cl. .......................................... 433/126; 433/125
[58] Field of Search ................................ 433/114, 116, 433/125, 126, 127, 128

[56] References Cited

U.S. PATENT DOCUMENTS

| | | |
|---|---|---|
| 186,471 | 1/1877 | Gilbert . |
| 186,504 | 1/1877 | Starr . |
| 307,686 | 11/1884 | Starr . |
| 1,522,757 | 1/1925 | Thiedemann . |
| 1,534,817 | 4/1925 | Thiedemann et al. . |
| 1,838,982 | 12/1931 | Angell . |
| 1,982,336 | 11/1934 | Wiseman . |
| 2,010,421 | 8/1935 | Terry . |
| 2,090,885 | 8/1937 | Clark . |
| 2,135,933 | 11/1938 | Blair . |
| 2,738,528 | 3/1956 | Fridge, Sr. . |
| 2,766,470 | 10/1956 | Baker . |
| 3,163,934 | 1/1965 | Wiseman . |
| 3,389,468 | 6/1968 | Lewis et al. . |
| 3,407,502 | 10/1968 | Richmond . |
| 3,472,045 | 10/1969 | Nelson et al. . |
| 3,672,060 | 6/1972 | Eibofner et al. . |
| 3,727,313 | 4/1973 | Graham . |
| 3,740,853 | 6/1973 | Brahler . |
| 3,798,777 | 3/1974 | Reiter . |
| 4,014,099 | 3/1977 | Bailey . |
| 4,021,918 | 5/1977 | Bailey . |
| 4,040,311 | 8/1977 | Page, Jr. et al. . |
| 4,053,983 | 10/1977 | Flatland . |
| 4,182,041 | 1/1980 | Girard . |
| 4,234,308 | 11/1980 | Leonard . |
| 4,253,832 | 3/1981 | Bailey . |
| 4,266,933 | 5/1981 | Warden et al. . |
| 4,285,671 | 8/1981 | Lustig et al. . |
| 4,292,027 | 9/1981 | Richmond . |
| 4,310,310 | 1/1982 | Bailey . |
| 4,365,956 | 12/1982 | Bailey . |
| 4,406,621 | 9/1983 | Bailey . |
| 4,449,932 | 5/1984 | Lustig . |

(List continued on next page.)

FOREIGN PATENT DOCUMENTS 328171  11/1919  Germany .

*Primary Examiner*—Nicholas D. Lucchesi
*Attorney, Agent, or Firm*—Polster, Lieder, Woodruff & Lucchesi

[57] ABSTRACT

A plastic, disposable, easy-to-assemble dental angle is provided. The angle includes a one-piece hollow body having a head at its front end which is angled with respect to the body. Both the head and the body have a bore therethrough. The head has an aperture which is centered with respect to the bore of the body to allow insertion of a drive gear through the head of the angle. A driven gear is inserted in the head from above. A snap cap fits within the head over the driven gear to lock both the drive gear and the driven gear in the angle. A sheath on the cap covers the aperture. A latch on the cap is received in the aperture to lock the cap to the head to hold the angle together. An elongated slot in the body permits the body to be force-fit on a dental handpiece. In an alternative embodiment, the length of the angle is shortened so that the thrust load produced during use is carried by a rolling contact in the handpiece to which the angle is secured, rather than by a sliding, friction-producing, contact between the drive gear's shaft and the surfaces of the angle itself. In a third embodiment, a simple, disposable contra-angle is provided.

25 Claims, 3 Drawing Sheets

U.S. PATENT DOCUMENTS

| | | |
|---|---|---|
| 4,533,324 | 8/1985 | Nakanishi . |
| 4,544,356 | 10/1985 | Gardella et al. . |
| 4,564,354 | 1/1986 | Rosenstatter . |
| 4,575,338 | 3/1986 | Maizenberg . |
| 4,604,058 | 8/1986 | Fisher . |
| 4,911,639 | 3/1990 | Jacklich . |
| 5,020,994 | 6/1991 | Huang . |
| 5,028,233 | 7/1991 | Witherby . |
| 5,040,978 | 8/1991 | Falcon et al. . |
| 5,040,979 | 8/1991 | Kuhn . |
| 5,040,980 | 8/1991 | Heil . |
| 5,090,904 | 2/1992 | Bailey . |
| 5,094,615 | 3/1992 | Bailey . |
| 5,120,220 | 6/1992 | Butler .................................... 433/125 |
| 5,156,547 | 10/1992 | Bailey . |
| 5,160,263 | 11/1992 | Meller et al. ........................... 433/125 |
| 5,224,859 | 7/1993 | Kraenzle . |

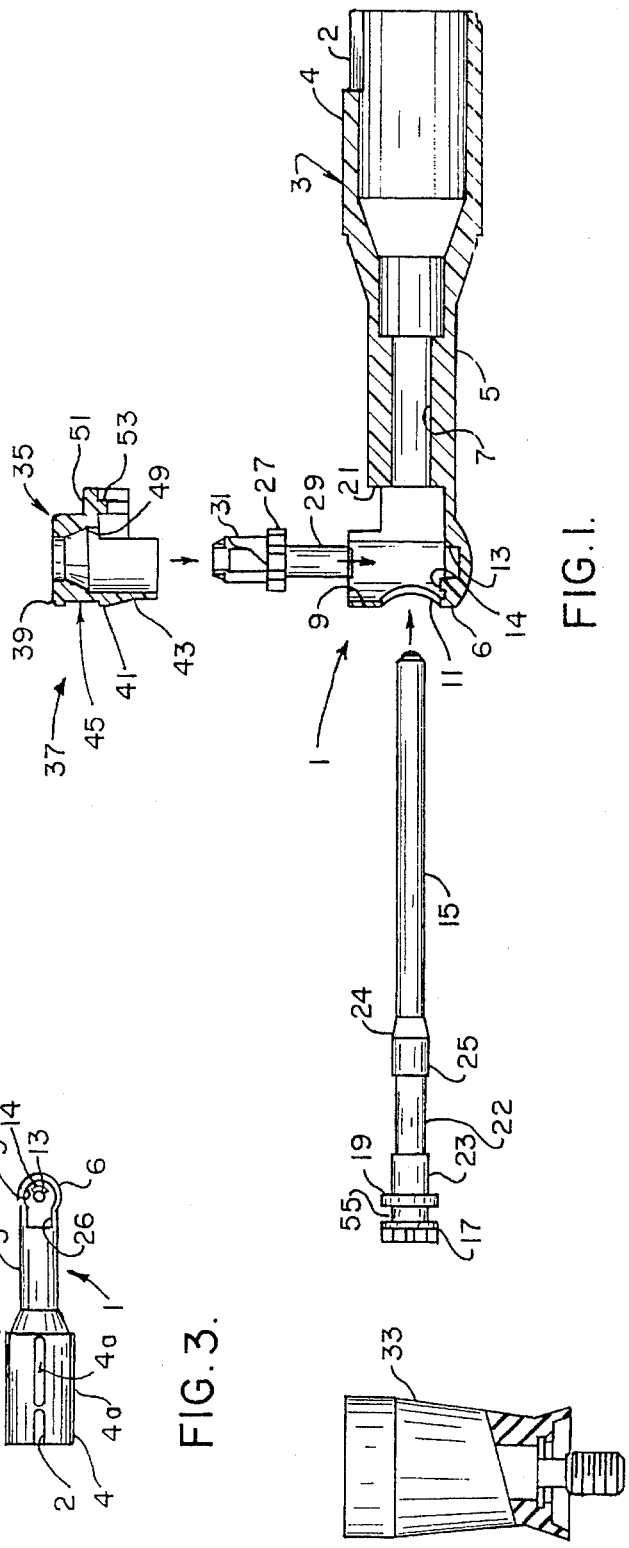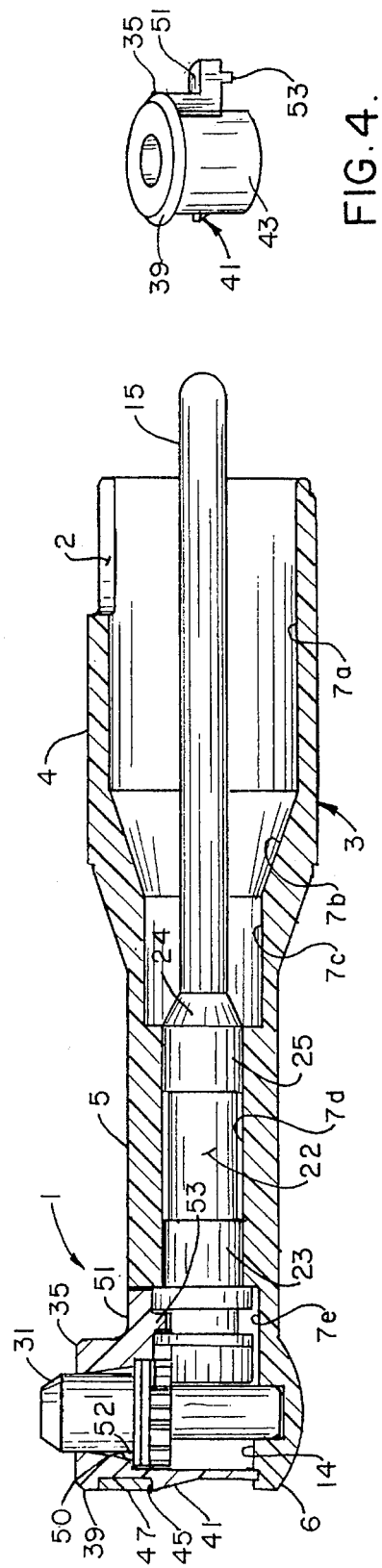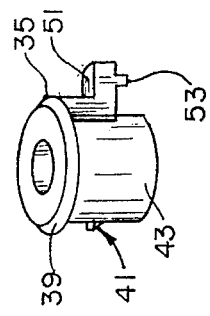

DENTAL PROPHYLAXIS ANGLE

CROSS-REFERENCE TO RELATED APPLICATIONS

This is a continuation of application Ser. No. 07/963,132, filed on Oct. 19, 1992, now U.S. Pat. No. 5,328,369, which is a continuation-in-part of application Ser. No. 07/613,366, filed Nov. 15, 1990, now U.S. Pat. No. 5,156,547.

BACKGROUND OF THE INVENTION

This invention relates to dental or prophylaxis angles, and, in particular, to a disposable dental angle and method of assembly.

Dental angles carry dental bits such as prophy cups and brushes and burs. The angle enables dentists to reach more easily the various surfaces of a patient's teeth and thus facilitates the cleaning of the teeth. These angles generally include a body having a head thereon which has a major axis angled relative to the major axis of the body. The angle is commonly 90°. A drive gear and a driven gear are carried in the body in a meshing relationship. The driven gear carries a desired dental bit, such as a cleaning cup or a brush, which is to be used during the cleaning procedure. The body is slipped over the nose of a handpiece such as a Doriot type handpiece having a collet which receives the shaft of the drive gear. The collet holds the shaft, hence the angle, against axial movement. It also connects the drive gear to a motor, to rotate the drive gear, and thus the dental bit.

The use of disposable dental angles reduces the labor, cost, and risks of sterilization.

Contra-angles are often used by dental personnel for getting to difficult spots. They are generally used in conjunction with burrs, but they may also be used with prophy cups. Contra-angles include a head which is angled at a greater angle than the usual 90° with respect to the axis of the handpiece. Typically the head is angled 10° to 30°, often 15° to 22°, from normal to the handpiece axis. In some designs, the body of the angle includes a 15°–22° angle formed in it; in others, an angled adapter is provided between the angle and the handpiece. To drive the dental bit secured to the head, contra-angles generally have two drive shafts. A first drive shaft extends from the bend to the Doriot to be grasped by the Doriot handpiece collet. It includes a gear at its forward end. A second drive shaft extends from the bend to the head. It includes a gear at its back end which meshes with the drive gear of the first shaft and a gear at its front end, which meshes with the gear at the end of the dental bit shaft to drive the dental bit. Contra-angles are therefore complex, expensive, and made of expensive materials. No satisfactory disposable contra-angle is presently known.

A first type of prior art disposable dental angle includes a two-piece body and is formed as a sandwich. The gears are placed in the first half of the body. The second half is then placed on top of the first half and the body is then joined such as by ultrasonic welding. However, when this type of dental angle is fitted over a collet of a Doriot handpiece, the forces exerted by the collet on the body tend to separate the body along its seams. Further, to avoid the possibility of welding the gears to the body when welding the body, the gears must fit loosely in the body. This leads to a loose fit between the gears and thus the gears do not run very smoothly.

A second type of prior art disposable angle includes a one-piece body which receives the drive gear from its rear such as is shown and described in U.S. Pat. No. 3,727,313 to Graham. A latch snaps in place behind a shoulder on the drive gear to lock the drive gear in place. However, the latch has a tendency to unhitch, allowing the drive gear to move axially within the body and to come out of contact with the driven gear. This frees the driven gear, allowing it to fall out of the head. This will cause obvious problems, especially if the latch comes undone during a cleaning procedure. The driven gear is positioned between the drive gear, and the head is thus held in place by the drive gear. Because the driven gear is placed below the drive gear, rather than above it, the dental bit rotates in an opposite direction from most other dental bits. This creates problems for hygienists who are accustomed to these other angles. During operation, the dental bit tends to "walk" due to the rotational contact with the tooth. A hygienist who has learned to compensate for "walk" in one direction, will have to become accustomed to compensating for "walk" in the opposite direction. There is, therefore, a "learning period" associated with this type of angle.

With either type of angle, the drive gear, particularly its shaft at the point where it narrows to its constant diameter, tends to overheat and fail.

SUMMARY OF THE INVENTION

One object of the invention is to provide a dental angle which is rugged and will not come apart.

Another object is to provide such a dental angle which runs smoothly and without overheating or failing, even for extended periods at high rotational speeds.

Another object is to provide such a dental angle which is easy to assemble.

Another object is to provide such a dental angle which is inexpensive to produce.

Another object is to provide such an angle which provides rotation in the conventional direction.

Another object is to provide a dental angle in which the thrust load produced during use of the angle is carried by a rolling contact, rather than a sliding contact.

Another object is to provide a disposable, inexpensive contra-angle having some or all of the foregoing advantages.

These and other objects will become apparent to those skilled in the art in light of the following disclosure and accompanying drawings.

In accordance with the present invention, generally stated, a disposable dental angle is provided comprising a one-piece body having an axial bore extending completely through it and a head integral with the body at one end thereof. The body bore extends through an exterior wall of the head, forming an aperture at the front of the head and aligned with the body bore. The head has an axial bore therein, at an angle to the body bore, terminating in a pilot bearing at the bottom of the head bore. A drive gear on a shaft is inserted into the body bore through the aperture, shaft first, and a driven gear is inserted through the head bore to be in meshing contact with the drive gear. The driven gear carries a dental bit, such as a prophy cup or brush.

The angle also includes a cap having locking means for locking the drive gear and the driven gear in place. The locking means comprises a latch on the cap which is received in the aperture. A sheath on the cap extending below the latch covers the aperture. The cap further includes a retaining shoulder which covers the driven gear to prevent vertical (axial) movement of the driven gear.

The body further includes a second aperture, extending rearwardly from the head, which exposes the drive gear. A circumferential flange on the drive gear shaft behind the drive gear forms a groove with the drive gear. The cap preferably includes a rear lip which covers the second aperture and which includes a downwardly extending finger which is received in the groove to prevent axial movement of the drive gear. The cap acts as a retainer, a shield, and a radial bearing.

The rear end of the body aperture is defined by a cylindrical sleeve or skirt part which is proportioned to form a friction fit with the nose of the Doriot handpiece. An axial slot in the skirt is longer than required to fit over a pin on the nose of the handpiece, to permit the skirt to expand sufficiently to form a tight, friction fit with the nose. The body of the angle is thus secured axially to the handpiece independent of the chuck holding the shaft of the drive gear. It has been found that one of the causes of heating and failure of conventional disposable angles is that the operator tends to push the body of the angle forward in use, thereby causing an axial load on the drive gear. The size-on-size fit of the present angle on the handpiece prevents movement of the angle's body with respect to the shaft, both axially and angularly, and thus reduces friction and heat in use.

In another embodiment, a dental angle comprising a body and a head which carries gears in a meshing relationship is provided. The body is mounted on a handpiece having drive means which receives a shaft of one of the gears to drive the gears. The distance between the head and the handpiece is sufficiently short that the load created when the dental bit is urged against a surface is transmitted to and substantially carried by the handpiece. The drive means preferably includes a collet or chuck which rotates on anti-friction ball bearings in the handpiece. The collet receives the gear shaft. The load is transferred along the shaft to the collet. The ball bearings provide a rolling contact between the collet and the handpiece so that the load is carried by the rolling contact.

In a third embodiment, a one-piece contra-angle is provided. The contra-angle has a body and body cavity which include a bent or curved axis, and a one-piece drive gear including a gear and a shaft. To enable the shaft to rotate along its bent axis, the shaft has a hollow portion formed at the front thereof and extending rearwardly to a point beyond the bend in the body.

The optional placing of silicone grease or other inert lubricant on the gears allows the gears to be operated at speeds in excess of 3,000 rpm. This allows for the use of drill bits on the angle.

BRIEF DESCRIPTION OF THE FIGURES

FIG. 1 is an exploded view, partially in cross section, of an angle of the present invention;

FIG. 2 is a cross-sectional view of the angle of FIG. 2, assembled;

FIG. 3 is a bottom plan view of a body of a dental angle of the present invention;

FIG. 4 is a perspective view of a snap cap used to lock the components of the angle in the body;

DESCRIPTION OF THE PREFERRED EMBODIMENT

Figure 5:
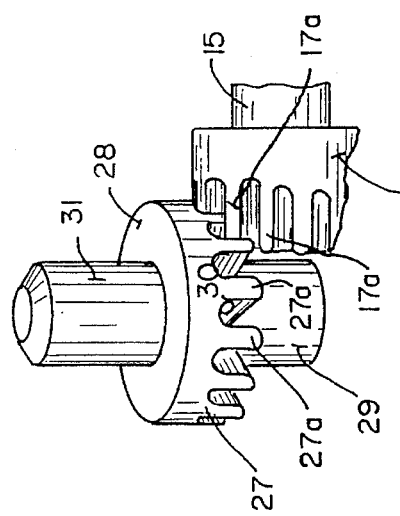
FIG. 5 is perspective view of a drive gear and a driven gear in meshing contact.

Referring to FIGS. 1–3, reference numeral 1 generally indicates a dental angle of the present invention. Angle 1 includes a one-piece body 3, a drive gear 17, a driven gear 27, and a cap 35. All the pieces are preferably molded of plastic so that angle 1 will be inexpensive to produce and thus disposable. This eliminates the need to sterilize angles and their associated bits between uses and thus eliminates any problem of cross-contamination between patients. It has been found that when dissimilar plastics are used for the body, cap, and gears, the angle operates more smoothly. Thus, it is preferred that the body and cap be made from a hard plastic such as a polycarbonate resin available from General Electric Co. under the trademark LEXAN, and that the gears be made from a more flexible plastic, such as a self-lubricating acetal copolymer available from Celanese Corp. under the trademark CELCON.

Body 3 includes a sleeve 4, a neck 5, and a head 6 formed integrally therewith. Sleeve portion 4 is formed as a cylinder, having thin reinforcing ribs 4a. (FIG. 3) The wall thickness of the sleeve 4 is about 0.04". A slot 2 at the rear, open, end of the sleeve 4 is about 0.250" long and about 0.1" wide. The slot 2 is about twice as long as necessary to accommodate a standard positioning pin or finger on a standard Doriot type handpiece. The length of the slot 2 and the thinness of the plastic sleeve wall in which it is formed permit the sleeve to expand slightly when it is forced onto a Doriot handpiece. The forward end of the sleeve portion 4 tapers to the neck portion 5, which is a smaller diameter cylinder coaxial with the sleeve 4. The head portion 6 is formed as a cylinder at right angles to the neck 5, with the axis of the head 6 intersecting the axis of the neck 5.

Body 3 and head 6 have axial bores 7 and 9, respectively.

Body bore 7 is formed with several diameters. In the sleeve portion 4, bore 7a is formed with the same diameter as the nose of a standard Doriot handpiece. It tapers as at 7b in the transition between sleeve 4 and neck 5, to a smaller diameter portion 7c in the neck 5, then steps to a yet smaller diameter portion 7d through the forward part of the neck 5. The portion 7d acts as a journal for the drive gear shaft, as described hereinafter. Forward of the small diameter portion 7d, the bore 7 steps to a larger diameter portion 7e, extending through the head portion 6 and forming an aperture 11 in the forward end of the head 6.

Head bore 9 is formed at a 90° angle with respect to body bore 7. At the lower end of the head 6 head bore 9 forms a blind hole 13 centered with respect to the head bore 9. A crescent-shaped rib 14 on the forward side of the blind hole 13 is spaced a short distance from the forward wall of the head.

Figure 6:
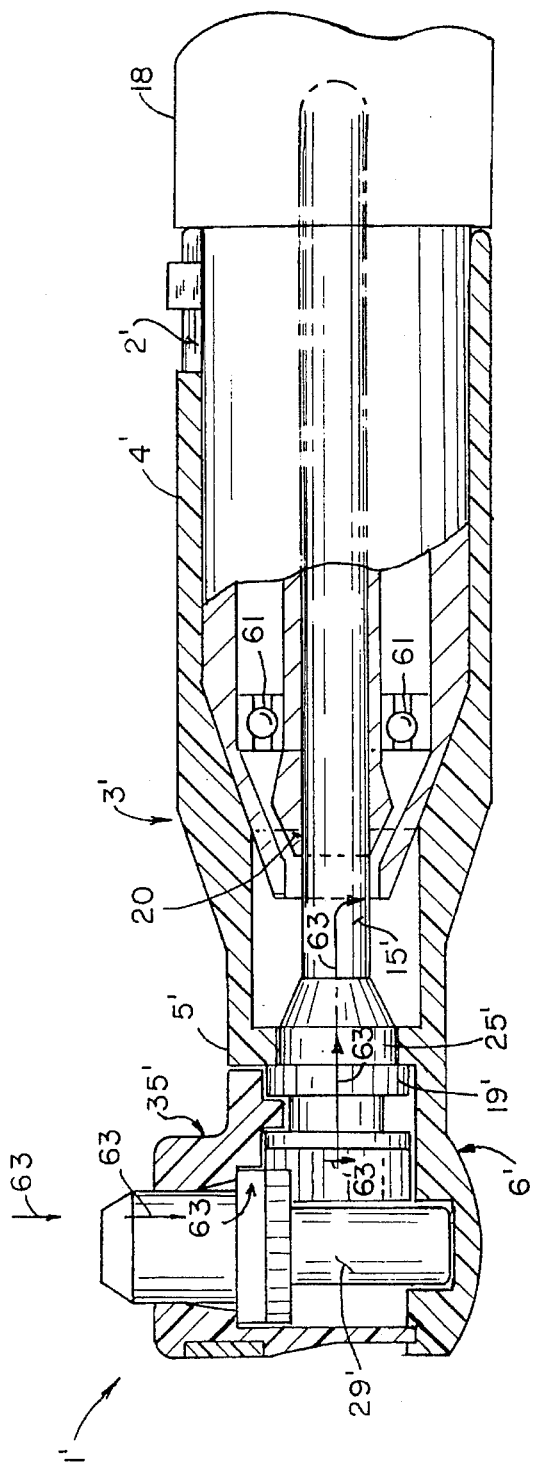
FIG. 6 is a cross-sectional view of a second embodiment of the present invention.

Drive gear 17, which is fixed to one end of a drive gear shaft 15, is received in body bore 7 through aperture 11. Shaft 15 extends beyond the end of body 3 when inserted therein to facilitate the capture of drive shaft 15 by chuck jaws 20 in a handpiece 18, such as a collet 20 in a Doriot handpiece (FIG. 6). Collet 20 holds shaft 15 so that it may be driven by an air motor in handpiece 18, as is well known in the art.

A flange 19 on shaft 15, spaced behind gear 17, butts up against a shoulder 21 in body 3 to properly position shaft 15 and hence gear 17 in body 3. About 0.125" behind the flange 19, the shaft 15 is slightly relieved for about 0.250", as indicated at 22, to form a forward bearing surface 23 and a rear bearing surface 25. The bearing surfaces 23 and 25 form a smoothly rotatable fit with the forward and rearward portions of the neck portion 7d of the body bore 7. A conical section 24 behind the rear bearing surface 25 provides a transition to a smaller-diameter rearward stem section of the shaft 15. The conical section 24 reinforces the stem 15 at its weakest point and helps to transfer heat from the bearing section 25.

When properly positioned, gear 17 is slightly behind blind hole 13. A rectangular opening 26 on body 3 at the junction of the head 6 and sleeve 5 exposes gear 17 and flange 19.

Driven gear 27, which is fixed to a shaft 29, is received in head bore 9. Blind hole 13 receives shaft 29 to center gear 27 in head bore 9. When inserted in head bore 9, driven gear 27 meshes with drive gear 17 to be driven thereby. Drive gear 17 does not contact shaft 29. A boss 31 on top of driven gear 27 receives a dental bit, such as a prophy cup 33.

As can be seen in FIG. 5, the gears 17 and 27 form a 90° cog gear system. The teeth 27a of gear 27 preferably do not extend all the way through the gear. Rather, the gear has a planar cap 28 above teeth 27a. Further, the spaces 30 between the tops of teeth 27a are contoured. Because gear teeth 17a of gear 17 radiate outwardly from the root of gear 17, the teeth 27a do not extend into the spaces between teeth 17a to the point where the width of the space between teeth 17a is equal to the width of tooth 27a. Thus, the contact between gears 17 and 27 occurs in the space 30 between teeth 27a, rather than in the root of drive gear 17. This creates a rolling contact between the gears, allowing the gears to run more smoothly.

A snap cap 35 (FIG. 4) is received in head bore 9 to lock gears 17 and 27 and their associated shafts in place in body 3. At its forward end 37, cap 35 includes a lip 39, a latch 41 and a sheath 43. The lip 39 and sheath 43 extend about 280° around the front of the cap 35. Sheath 43 has an outer diameter equal to the diameter of the head bore 9 and fits snugly into the head bore 9. Lip 39 and latch 41 define a section 45 of sheath 43 which is sufficiently wide to fit around a portion 47 of head 6 between aperture 11 and the top of head 6. Latch 41 slopes upwardly and outwardly from sheath 43. Thus, when cap 35 is inserted into head 6, head portion 47 is urged outward until the cap is in place. Portion 47 then snaps back above latch 41 securely locking snap cap 35 into place such that it is difficult to remove. Lip 39 extends over the top of head portion 47 and thus aids in preventing vertical movement of cap 35 to help lock the cap in place. Sheath 43 covers aperture 11 to prevent cleaning abrasive or other substances from entering head 6 during use. The free lower end of the sheath 41 fits into the space between the head bore 9 and the crescent rib 14 adjacent the blind hole 13.

To limit vertical movement of driven gear 27, cap 35 includes an annular shoulder 49 which accommodates gear 27. Planar surface 28 of gear 27 contacts shoulder 49, presenting a smooth contact between the two pieces rather than the non-continuous, possibly irregular surface which would be presented if teeth 27a extended the height of gear 27. Boss 31 extends above cap 35 to receive dental bit 33. The inner surface 50 of cap 35, which surrounds boss 31, tapers away from boss 31 to create a space 52 between boss 31 and surface 50. This space reduces the friction creating area between boss 31 and surface 50 allowing for smoother operation of the angle. It also creates an area through which cleaning abrasive may fall, thereby reducing galling caused by the action of the abrasive which enters head 6.

At its rear, cap 35 includes a lip 51 which fills body aperture 26. Lip 51 includes a downwardly extending finger 53 which fits in a groove 55 formed by drive gear 17 and flange 19 to prevent axial movement of gear 17 and shaft 15. Thus, gear 17 will not impinge on driven gear shaft 29, as previously noted.

To assemble angle 1, drive gear 17 and its associated shaft 15 are inserted, shaft first, into body 3 through aperture 11 until the flange 19 abuts the shoulder 21. Driven gear 27 is then inserted into head 6 from above the head until it meshes with gear 17. Cap 35 is then placed into head 6, closing up the assembly and locking the gears in place. A desired dental bit may then be inserted into boss 31 and the angle may be connected to the handpiece. As previously noted, the sleeve 4 forms a size-on-size fit with the nose of the handpiece, the extended slot 2 permitting the free end of the sleeve to expand sufficiently for easy mounting. The body 3 of the angle 1 therefore does not move axially or angularly during use and is held onto the handpiece independent of the capture of the stem 15 by the collet of the handpiece.

A second embodiment of the angle is shown in FIG. 6 and is designated 1'. Angle 1' is substantially similar to angle 1. However, body 3' has a substantially shorter neck 5' than the neck 5 of angle 1. Further, drive gear shaft 15' has only one bearing surface 25', located behind flange 19' at the entrance to sleeve 5'. Angle 1' has the advantage of transferring the load produced during use to collet 20 rather than to a friction creating surface as in angle 1. Collet 20 rotates on anti-friction ball bearings 61 in handpiece 18. The load is thus carried by a rolling contact rather than a sliding, friction-producing contact, allowing for an easier rotation of gear 17.

In angle 1', the load follows the path shown by arrows 63. The load initially bears down on driven gear 27 and is transferred to drive gear 17. The load then is transferred axially along drive gear shaft 15' to collet 20 which rotates on ball bearings 61 in handpiece 18. There are gaps between driven gear shaft 29' and head blind hole 13', between flange 19' and cap 35' and head 6', and between drive gear shaft sleeve 25' and body sleeve 5'. Therefore, there is no sliding contact between the gears and the body in angle 1' and all the load is carried by collet 20. In contrast, in angle 1, the load is transferred to bearings 23 and 25 and the bore 7d in neck 5 through driven gear 27, drive gear 17 and shaft 15. Therefore, shortening neck 5 to the length of neck 5' enhances the operation of dental bit 33 by substantially reducing the friction bearing surfaces along which the load forces are transmitted. Neck 5' is preferably shortened by a length equal to the distance between the front of shaft bearing 23 and the front of shaft bearing 25 (i.e., 0.375"), so that sleeve 25' is adjacent shaft flange 19'.

When either of the angles 1 or 1' is assembled, it has been found that if a little bit of silicone grease is placed on gears 17 and 27 and in relieved area 22, the angle can operate at speeds upward of 7,000 rpm for extended periods of time. At speeds upward of 20,000 rpm, the gears operate for only a few minutes before melting. The ability of the gears to operate at such high speeds allows for drill bits to be used with the disposable angle. This allows the same sterile advantages obtained by disposable angle and prophylaxis cup assembles to be obtained by drill bits.

Figure 7:
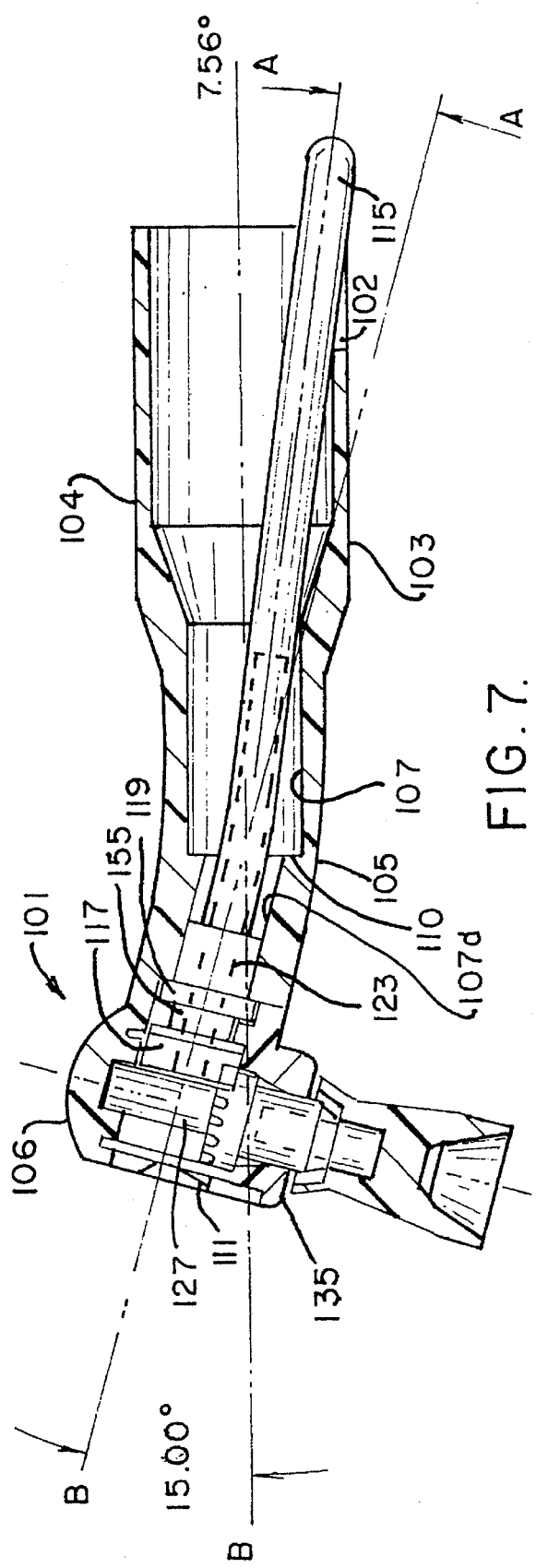
FIG. 7 is a cross-sectional view of a disposable contra-angle having a single drive shaft.
Figure 8:
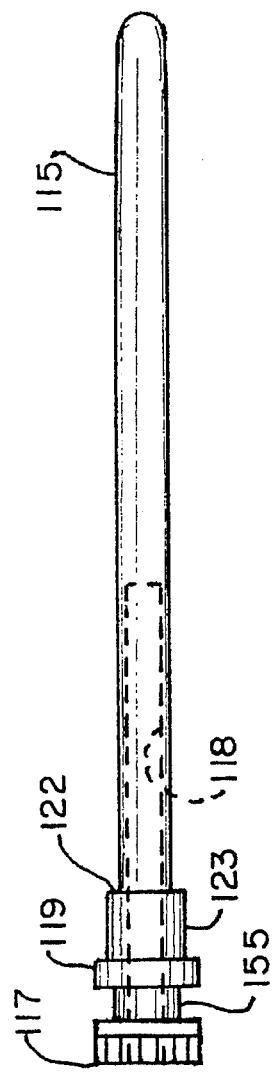
FIG. 8 is a view of the contra-angle's drive shaft.

A contra-angle 101 is shown in FIGS. 7 and 8 which incorporates the invention described above. Contra-angle 101, like angle 1 or 1', is a disposable angle made of plastics and incorporates a plastic drive gearing system. Contra-angle 101 has a one-piece body 103, a drive gear 117, a driven gear 127, and cap 135.

The driven gear 127 and cap 135 are identical with the driven gear 27 and cap 35 of the first embodiment.

Body 103 includes a sleeve 104, a neck 105, and a head 106. Head 106 is similar in construction to head 6 and has an opening 111 at its front through which drive gear 117 is passed. Sleeve 104 is identical in construction with sleeves 4 and 4' and includes a slot 102 at the rear, open, end of the sleeve 104. The construction of body 103 differs from that of body 3 in that neck 105 defines an angle of about 15°, as at 110, from the horizontal. Bore 107, within neck 105 has a matching angle.

As in the first and second embodiments, drive gear 117 is formed integrally with a drive gear shaft 115. Drive shaft 115 includes a shoulder 119 spaced from the back of gear 117, defining a channel 155. Shaft 115 is stepped as indicated at 122 to define a single bearing surface 123 behind shoulder 119. The bearing surface 123 forms a smoothly rotatable fit with the forward portion of the neck portion 107d of the body bore 107. The remainder of the shaft 115 is of constant outer diameter.

To provide the shaft 115 with additional flexibility, the forward end of the shaft, from gear 117 to a point beyond the area of maximum flexion of the shaft is provided with an axial cavity 118. The constant diameter rearward portion of the shaft 115 has an outer diameter of 0.0935", and the cavity 118 has a diameter of 0.0620" and a depth of 0.875".

If shaft 115 were solid, it could bend to pass through angled bore 107d, but it would be less able to rotate about its axis effectively. When the shaft 115 is bent, it constantly has a compressed surface and a stretched surface opposite the compressed surface. When the shaft 115 rotates, the compressed and stretched surfaces are constantly changing. Thus, the surface of the shaft must be able to accommodate the constant change in stress placed upon it by the bend. The axial cavity 118 provides the shaft 115 with this pliability.

Contra-angle 101 is assembled in the same manner as angle 1. The bearing 123 is lubricated. The drive gear 117 and its shaft 115 are inserted into body 103 shaft first. The driven gear is then inserted into head 106 and the assembly is closed with cap 35. When shaft 115 is inserted into body 103, it stays generally straight. As shown in FIG. 7, the rearward end of the shaft 115 naturally extends into the slot 102 in the skirt 104, thereby reducing further the amount of bend in the shaft 115 during shipment and storage of the angle 101 to about 7.5°. The shaft thus stays in a relatively relaxed position until it is ready for use, which can be a considerable time after assembly.

When the angle 101 is to be used, the shaft 115 is inserted into the collet of the handpiece, as is shown in FIG. 6. Not until then does the shaft conform fully to the angle of neck 105. Because the shaft remains in its relaxed state until use, the shaft will not take a set. If the shaft were to be in its bent, flexed state from the time of assembly, the bend would tend to become set in the shaft. This would prevent contra-angle 101 from rotating smoothly and would greatly shorten the life of the shaft 115. By remaining in its relaxed, generally straight, position, the shaft remains more pliable, enabling it to take a constantly changing bend along its surface during use of the angle 101. The embodiment of FIGS. 7 and 8 has been run at 3,000 rpm for six hours before the shaft broke. This is far in excess of the time of use of the contra-angle on a single patient.

It will be seen that although the use of the shaft 115 in the preferred construction of contra-angle provides many advantages, a similar shaft with a hollow portion to provide flexibility could be used in modifications of other types of disposable prophylaxis angles to provide a disposable contra-angle.

Numerous other variations, within the scope of the appended claims, will be apparent to those skilled in the art in light of the foregoing description and accompanying drawings.

I claim:

1. A disposable dental prophylaxis angle for attachment to a dental handpiece, the dental handpiece including a nose part and a chuck within the nose part, the dental angle comprising:

a one-piece plastic body including a sleeve with an open rear end sized to be received on the handpiece nose, a neck extending from said sleeve, a head including a back extending from said neck and an open front, a body bore extending through said sleeve and said neck, said body bore having a reduced diameter portion in said neck smaller than a diameter of said body bore in said sleeve;

a one-piece plastic drive part including a shaft and a drive gear on said shaft, said shaft extending through said body bore to be received by said chuck, said drive gear having a diameter greater than said reduced diameter portion of said body bore, said drive gear being sufficiently small that said drive part may be inserted shaft first through said open front of said head into said body bore;

a one-piece plastic driven part rotatably mounted in said head and operatively connected to said drive part to be driven by said drive gear, said driven part including a driven gear;

a cleaning bit mounted on said driven part for rotation therewith; and a plastic cap mounted to said head, said cap closing said open front of said head.

2. The dental angle of claim 1 wherein a back of said drive gear is in abutting relationship with said head back to prevent rearward movement of said drive part with respect to said body.

3. The dental angle of claim 2 wherein said drive gear includes a toothed gear and a flange spaced rearwardly of said toothed gear, said flange abutting said back of said head.

4. The dental angle of claim 3 wherein said toothed gear and flange define a groove between them, said cap including a projecting part extending into said groove for restricting axial movement of said drive gear relative to said body bore.

5. The dental angle of claim 1 wherein said cleaning bit is mounted to an upper end of said driven part, said cap defining at least a part of an opening through which said upper end of said driven part extends.

6. The dental angle of claim 5 wherein said cap defines an upper bearing limiting axial and radial movement of said driven part.

7. The dental angle of claim 1 wherein said head defines a forward wall, said forward wall defining an opening in axial alignment with said body bore.

8. The dental angle of claim 7 wherein said cap includes means for forming an interference snap fit with said opening.

9. The dental angle of claim 1 wherein said cap is snap fitted to said head.

10. A disposable dental prophylaxis angle for attachment to a dental handpiece, the dental angle comprising:

a one-piece plastic body including a sleeve with an open rear end sized to be received on the handpiece and a head including a back adjacent said sleeve and an open front, a body bore extending through said sleeve, said body bore having a reduced diameter portion adjacent said head;

a one-piece plastic drive part including a shaft and a drive gear on said shaft, said shaft extending through said body bore to said open rear end, said drive gear extending into said head, said drive gear having a diameter greater than said reduced diameter portion of said body bore, said drive gear being sized to permit said drive part to be inserted shaft first through said open from of said head into said body bore;

a plastic cap mounted to said head, said cap closing said open front of said head;

a one-piece plastic driven part rotatably mounted in said head and operatively connected to said drive gear, said driven part including a driven gear meshing with said drive gear, said cap and said head enclosing said driven gear and forming upper and lower bearings for said driven part; and a cleaning bit mounted on said driven part for rotation therewith.

11. The dental angle of claim 10 wherein said cleaning bit is mounted to an upper end of said driven part, said cap defining at least a part of said upper bearing and forming at least a part of an opening through which said upper end of said driven part extends.

12. The dental angle of claim 11 wherein said lower bearing in said head is at least partially formed in said one piece body.

13. The dental angle of claim 10 wherein said cap is snap fitted to said head.

14. A method of assembling a disposable dental angle including a one-piece hollow plastic body having a sleeve and a head, a drive part and a driven part, said method comprising:

inserting said drive part into said body through an open front of said head, said drive part including a shaft and a gear larger than said shaft, said drive part being inserted shaft first until said gear seats against a bearing in said sleeve;

thereafter, inserting a driven gear into said head until said driven gear is in meshing contact with said drive gear and locking said drive gear and said driven gear in said angle by means of a plastic cap snapped to said head to close said open front of said head.

15. The method of claim 14 including a step of mounting a cleaning bit to said driven gear for rotation therewith.

16. In a dental angle comprising a plastic body including a sleeve and a head, the sleeve including at least a first bearing and the head including a chamber having an upper bearing and a lower bearing; a one-piece plastic drive part mounted in the sleeve, the drive part including a drive gear extending into the head and a shaft mounted for rotation in the first bearing; a one-piece plastic driven part including a driven gear operatively driven by said drive gear, a first shaft rotatably mounted in said lower bearing in a lower part of the head, and a boss extending through said upper bearing in the head, the boss carrying a dental tool, the improvement wherein said sleeve and a part of said head are formed in one piece, wherein said head further comprises a plastic cap snap-fitted to said one piece, wherein said lower bearing in said head is at least partially formed in said one piece, and wherein said upper bearing is at least partially formed in said cap.

17. The improvement of claim 16 wherein said drive part is inserted shaft first into said first bearing in said sleeve through said head, said gear being larger than said first bearing.

18. In the combination of a dental handpiece and a dental angle mounted on the handpiece, the handpiece comprising a nose terminating in a shoulder, the nose including a frustoconical part and a cylindrical part, a projection on the cylindrical part for angularly aligning the dental angle, and a chuck within the nose part, the angle comprising a body including a sleeve with an open rear end abutting said shoulder, a head, and an axial bore extending through the sleeve to the head, the axial bore including a reduced diameter part; a drive gear including a gear part and a shaft part, said shaft part extending rotatably through said first bore and being held by said chuck; and a driven gear rotatably mounted in said head and operatively connected to said drive gear, said driven gear carrying a dental bit;

the improvement wherein the angle body is formed of plastic in one piece, wherein the drive gear is formed in plastic in one piece, wherein the sleeve of the angle body includes a generally axial slot at its open end, the slot extending substantially forward of the projection on the handpiece when the angle is mounted on said handpiece with the open rear end of the sleeve against the shoulder on the handpiece nose, the length of the slot and the thinness of the plastic sleeve permitting the sleeve to expand sufficiently when it is forced onto the handpiece to form a size-on-size friction fit with the cylindrical part of the handpiece nose and hold the angle body positioned angularly and axially with respect to the handpiece substantially independent of the shaft part's being held by the chuck, and wherein the gear is larger than the reduced diameter part of the axial bore in the body, the size of the gear limiting axial movement of the body away from the handpiece when the shaft part is held by the chuck, substantially independent of the body's being held by the handpiece nose.

19. The combination of claim 18 wherein said head receives said drive gear shaft first, said angle further including a plastic cap mounted to said head, said cap closing said head and locking said driven gear in said angle.

20. The combination of claim 19 wherein said cap is snap fitted to said head.

21. In a disposable dental prophylaxis angle for attachment to a dental handpiece, the dental handpiece including a nose part and a chuck within the nose part, the dental prophylaxis angle comprising:

a body having a sleeve with an open rear end sized to be received on the handpiece nose, a neck extending forwardly from the sleeve, a head extending forwardly from the neck, and a body bore extending through the sleeve and the neck, the body bore having a reduced diameter portion in the neck smaller than a diameter of the body bore in the sleeve;

a drive part including a shaft and a drive gear on the shaft, the shaft extending through the body bore to be received by the chuck, the drive gear having a diameter greater than the shaft;

a driven part, the driven part including a driven gear housed in the head in operative connection with the drive gear; and a prophylaxis tool carried by the driven part for rotation with the driven gear, the improvement wherein the body comprises a one-piece plastic body part, including the sleeve, the neck, at least a part of the head, and the body bore, a forward end of the reduced diameter portion of the body bore forming a forwardly facing shoulder in the one-piece body part, the at least a part of the head including a forwardly-opening aperture in axial alignment with the body bore, the aperture being at least as large as the drive gear on the drive part and being sized and proportioned to permit the drive part to be inserted shaft first into the body bore to an operative position with a back of the drive gear in abutting relationship with the forwardly facing shoulder of the one-piece body part to prevent rearward movement of the drive part with respect to the body.

22. The improvement of claim 21 wherein the head part of the one-piece body includes a thrust bearing surface and wherein the driven part includes a bearing surface engaging the thrust bearing surface of the head part.

23. In a disposable dental prophylaxis angle for attachment to a dental handpiece, the dental handpiece including a nose part and a chuck within the nose part, the dental prophylaxis angle comprising:

a body having a sleeve with an open rear end sized to be received on the handpiece nose, a neck extending forwardly from the sleeve, a head extending forwardly from the neck, and a body bore extending through the sleeve and the neck, the body bore having a reduced diameter portion in the neck smaller than a diameter of the body bore in the sleeve;

a drive part including a shaft and a drive gear on the shaft, the shaft extending through the body bore to be received by the chuck, the drive gear having a diameter greater than the shaft;

a driven part, the driven part including a driven gear housed in the head in operative connection with the drive gear; and a prophylaxis tool carried by the driven part for rotation with the driven gear, the improvement wherein the body comprises a one-piece plastic body part, including the sleeve, the neck, at least a part of the head, and the body bore, a forward end of the reduced diameter portion of the body bore forming a forwardly facing shoulder in the one-piece body part;

wherein the drive part is formed in one piece, the drive part being sized and proportioned to permit the drive part to be inserted shaft first into the body bore to an operative position with a back of the drive gear in abutting relationship with the forwardly facing shoulder of the one-piece body part to prevent rearward movement of the drive part with respect to the body; and further including a plastic cap mounted to the head part of the one-piece body, the cap closing the head.

24. A method of assembling a dental prophylaxis angle for attachment to a dental handpiece, the dental handpiece including a nose part and a chuck within the nose part, the dental prophylaxis angle comprising:

a body having a sleeve with an open rear end sized to be received on the handpiece nose, a neck extending forwardly from the sleeve, a head extending forwardly from the neck, and a body bore extending through the sleeve and the neck, the body bore having a reduced diameter portion in the neck smaller than a diameter of the body bore in the sleeve;

a drive part including a shaft and a drive gear on the shaft, the shaft extending through the body bore to be received by the chuck, the drive gear having a diameter greater than the shaft;

a driven part, the driven part including a driven gear housed in the head in operative connection with the drive gear; and a prophylaxis tool carried by the driven part for rotation with the driven gear, the method comprising forming the body as a one-piece plastic body part, including the sleeve, the neck, at least a part of the head, and the body bore, a forward end of the reduced diameter portion of the body bore forming a forwardly facing shoulder in the one-piece body part;

the method further comprising a step of inserting the drive part shaft first through the head part of the body into the body bore to an operative position with a back of the drive gear in abutting relationship with the forwardly facing shoulder of the one-piece body part to prevent rearward movement of the drive part with respect to the body, and thereafter a step of inserting the driven part into the head part until the driven gear is in operative engagement with the drive gear.

25. The method of claim 24 further comprising a step of snap fitting a plastic cap to the head part of the one-piece body to lock the drive part and the driven part in the body.

* * * * *